United States Patent
Zhang

(10) Patent No.: US 9,023,817 B2
(45) Date of Patent: May 5, 2015

(54) USE OF ALBIFLORIN FOR ANTI-DEPRESSION

(76) Inventor: Zuoguang Zhang, Chaoyang Beijing (CN)

(*) Notice: Subject to any disclaimer, the term of this patent is extended or adjusted under 35 U.S.C. 154(b) by 224 days.

(21) Appl. No.: 13/502,880

(22) PCT Filed: Aug. 24, 2010

(86) PCT No.: PCT/CN2010/076279
§ 371 (c)(1),
(2), (4) Date: Jul. 6, 2012

(87) PCT Pub. No.: WO2011/047576
PCT Pub. Date: Apr. 28, 2011

(65) Prior Publication Data
US 2012/0270820 A1   Oct. 25, 2012

(30) Foreign Application Priority Data
Oct. 20, 2009  (CN) .......................... 2009 1 0180883

(51) Int. Cl.
*A61K 31/7048* (2006.01)
*A61K 9/00* (2006.01)
*A61K 9/20* (2006.01)
*A61K 9/48* (2006.01)

(52) U.S. Cl.
CPC ............ *A61K 31/7048* (2013.01); *A61K 9/0019* (2013.01); *A61K 9/2059* (2013.01); *A61K 9/4866* (2013.01)

(58) Field of Classification Search
CPC .......................... A61K 31/7048; A61K 36/65
USPC .................................. 514/27, 470
See application file for complete search history.

(56) References Cited

FOREIGN PATENT DOCUMENTS

| CN | 1256090 C | 11/2004 |
|---|---|---|
| CN | 100509006 C | 9/2006 |
| CN | 101062128 | 10/2007 |
| CN | 101332205 A | 12/2008 |
| CN | 101385736 A | 3/2009 |

OTHER PUBLICATIONS

"Depression", NHS Choices, Feb. 23, 2009, http://www.nursingtimes.net, accessed online Apr. 29, 2014.*
Entry for Depression, Mayo Clinic, http://www.mayoclinic.org, accessed online Apr. 29, 2014.*
Definition of prevent, Oxford English Dictionary Online, http://dictionary.oed.com/, accessed online Mar. 27, 2010, especially definition 9a. at p. 2.*
Mao et al., J. Ethnopharmacology, 2008, 119, p. 272-275.*
WHO Monographs on Selected Medicinal Plants—vol. 1: Radix Paeoniae, 1999, http://apps.who.int, accessed online on Apr. 28, 2014.*
Google Patents translation of Foreign Patent CN-101385736A, https://www.google.com/patents, accessed online on Apr. 28, 2014.*
Berge et al., J. Pharm. Sci., 1977, 66(1), p. 1-19.*
Abdel-Hafez et al., Chem. Pharm. Bull., 2001, 49(7), p. 918-920.*
"International Application No. PCT/CN2010/076279, International Search Report mailed Dec. 2, 2010", 10 pgs.
Jing, Xu, et al., "Establishment and evaluation of the model of chronic stress induced depression", Chinese Journal of Behavioral Medical Science, 2003, 12(1): 14-16, (2003), 14-17.
Yulan, Mo, "Overview of Pharmacological Studies on Total Glucosides of Red Paeony Root", Guangming Journal of Chinese Medicine (Chinese), vol. 24, No. 4 (with English abstract), (Apr. 2009), 782-784.

* cited by examiner

*Primary Examiner* — Jonathan S Lau
(74) *Attorney, Agent, or Firm* — Schwegman Lundberg & Woessner, P.A.

(57) ABSTRACT

A pharmaceutical composition containing albiflorin and use thereof in manufacturing medicaments for preventing and treating depression are provided by the present invention.

3 Claims, No Drawings

USE OF ALBIFLORIN FOR ANTI-DEPRESSION

PRIORITY CLAIM TO RELATED APPLICATIONS

This application is a national stage application under 35 U.S.C. §371 of PCT/CN2010/076279, filed Aug. 24, 2010, and published as WO 2011/047576 A1 on Apr. 28, 2011, which claims priority to Chinese Application No. 200910180883.8, filed Oct. 20, 2009, which applications and publication are incorporated herein by reference and made a part hereof in their entirety, and the benefit of priority of each of which is claimed herein.

FIELD OF THE INVENTION

The present invention relates to the medicaments or food supplement for preventing, ameliorating and/or treating the nerve system diseases with mood disorders, especially to the anti-depressant medicaments or food supplement.

BACKGROUND OF THE INVENTION

Depression is the major type of mood disorders. It is a syndrome mainly characterized in remarkable and continuous depressed mood. Depression is a commonly and frequently occurred disease endangering physical and psychological health of human, and is a primary spirit disease all over the world.

Main behaviours of depression are low-spirited, reduced interest, pessimism, retardation of thinking, lack of initiative, reproving self from crime, poor diet and sleep, worrying that they are suffering from various diseases, feeling discomfort in multiple places throughout the body, suicidal thoughts and behaviors in patients with severe symptoms.

Depression has the highest suicide rate in psychiatry. It has a high morbidity. Almost one of each five adults is patient with depression. Therefore, it is called the cold of psychiatry. At present, depression has become the second most important disease seriously burdening on people among the global diseases. It causes suffering to patients and their families and loss to the society other than other diseases. The primary cause to such situation is that the society lacks correct cognition to depression and prejudice makes the patients unwilling to receive psychiatric treatments. In China, only 5% of patients with depression receive the treatments. Many of patients can not receive timely treatments. Their conditions become deteriorated, and even there are serious consequences of suicide. In another aspect, because of lacking of related knowledges of depression, people mistake for the ones with depression symptoms as being disgruntled, and could not afford deserved comprehension and emotional support, which causes greater psychological stress to the patients and leads to further deterioration of conditions.

The increasing severity of depression trend, as well as the decline in psychological diathesis and the damage to the social function of the patients with mood disorders, has drawn widespread attention of various countries throughout the world. The demand for anti-depressant medicaments is increasing worldwide. The sales volume of such medicaments in global market annually grows at a rate of 16.2% in recent years. The control of depression and the development of anti-depressant medicaments have become one of the forefronts of research hotspots of the international pharmaceutical industry in modern times.

There are many therapeutic methods of depression, such as psychotherapy, sleep deprivation therapy, light therapy and electroconvulsive therapy and the like, but pharmacotherapy is still taken as principal method at present, simultaneously supplemented by psychotherapy. Nowadays, the major anti-depressant medicaments substantially include five categories: Selective Serotonin Reuptake Inhibitors (SSRIs), Noradrenalin and Specific Serotonin Antagonist (NaSSA), Tricyclic Anti-depressants (TCAs), Monoamine Oxidase Inhibitors (MAOIs), and Serotonin and Noradrenalin Reuptake Inhibitor (SNARI). All of these drugs have adverse effects to different extents, such as somnolence, bluffed vision, hypertension, convulsions, hyposexuality and the like, which affects the extensive promotion thereof. Moreover, due to the limitation of the deficiencies of these drugs themselves, there are problems including narrower anti-depressant spectrum, more severe toxicities and side effects, expensive price, easy to relapse after drug withdrawal, not suitable for the recuperative treatment. Therefore, the clinical use of there drugs is significantly affected.

For example, there are anti-depressant drugs, Prozac, Seroxat, Zoloft and other serotonin reuptake inhibitors (SSRIs) in the domestic and foreign markets, whose mechanism of action is to ameliorate the symptoms of depression by increasing the content of serotonin component in the neurotransmitters of human bodies. All of these drugs have side effects to different extents, as proved by study, "the FuAn-Shuan contained in these drugs plays a role in balancing the human skills, but more often, they still can not make patients calm down". Moreover, these anti-depressant drugs cause serious social problems and possess potential safety hazard, for example, taking Seroxat results in increased suicidal tendencies in adolescents.

Depression is a clinical syndrome, which has many inducements and is the coefficient result caused by various factors. It is often difficult to achieve satisfactory results when treating with targeting a certain single link (target) only. However traditional Chinese medicine treatments pay attention to the comprehensive diagnosis and the overall regulation of various physiological systems in order to achieve the purpose of treatment. For example, as reported in a great number of documents, the formulations of *Bupleurum tenue* Decoction, *Pinellia ternata* Decoction, and BaiJinTang were used to treat "globus hysteriocus", "depression", and "depressive psychosis". Hu Sirong employed Ping Xin Wang You Decoction (magnetite, chlorite schist, *Fructus aurantii immaturus, Phellodendron amurense, Pinellia ternata, Magnolia officinalis, Poria cocos* mixed with powdered vermilion, ShenRou, *Cinnamomum aromaticum, Folium Perillae, Acorus calamus, Zingiber officinale*) to treat 470 cases of depression, 70.2% of which was recovered, 20.2% was improved, the total effective rate was 90.4%. Traditional Chinese medicine, "YiLvKang" capsules self-produced by Zhao Zhisheng were applied for the treatment of depression with better therapeutic effects in total than the control group of western medicine. Ma Yunzhi et. al., employed ShuYuTiaoShen Decoction (*Bupleurum chinensis, Curcuma aromatica, Acorus calamus, Fructus aurantii immaturus, Semen persicae, Carthamus tinctorius, Semen Boitae, Polygala chinensis*, calcinated fossil fragments and *Concha ostreae, Salvia miltiorrhiza*) to treat depression after stroke, cure rate of which was 39.06%, effectual rate was 30.40%, effective rate was 21.09%, ineffective rate was 9.45%, and the primary and concurrent symptoms were significantly improved. Japanese Ozaki Tetsuo found that XiaoJianZhong Decoction (*Ramulus cinnamomi, Zingiber officinale, Paeonia lactiflora, Glycyrrhiza uralensis, Fructus Zizyphi*, powdered maltose) had regulation effect to the emotions of patients with depressive neurosis. There are many clinical cases like these. However, compound Chinese herbal formulations still have the problems of effecting to be slow, nonsignificant effect, more complex components, unclear active ingredients and the like, hence the controllability of their qualities is restricted, and it is hard to use modern pharmacology to analyze their mechanisms of actions.

Recently, the studies on extracting monomer drugs with high anti-depressant activities from the traditional medicines are progressively increased, and have become the trend of the international pharmaceutical industry to develop the anti-depressant drugs. For example in Germany, hypericin extracted from *Hypericum perforatum* is employed for the treatment of depression. It not only has significantly effect, but also cause low side effects. Hence it falls into the scope of major anti-depressant drugs in European and American countries.

There are numerous anti-depressant studies on the monomer drugs from the traditional compound Chinese medicines and the extracts of Chinese medicines, for example:

Inventive patent application publication No. CN100509006C (authorized announcement number) discloses a pharmaceutical composition comprising *Panax ginseng, Glycyrrhiza uralensis*, and *Fructus zizyphi*, or the water extracts or ethanol extracts thereof for the treatment of depression.

Inventive patent application publication No. CN1256090C (authorized announcement number) discloses the use of *Centella asiatica* and the derivatives thereof for the preparation of anti-depressant medicaments.

Inventive patent application publication No. CN101385736A (publication number) discloses use of paeoniflorin in the medicaments for the prevention and treatment of depression, as well as the pharmaceutical composition thereof, said pharmaceutical composition contains an effective dose of paeoniflorin with pharmaceutically acceptable carriers, and can be prepared into a conventional liquid or solid dosage forms.

Inventive patent application publication No. 101332205A (publication number) discloses an anti-depressant drug using paeoniflorin as raw material, as well as the dosage thereof.

Albiflorin is a monoterpenoid compound, with the molecular formula of $C_{23}H_{28}O_{11}$ and the molecular weight of 480.46. The molecular structure thereof is shown as Formula (I). It is a natural active substance derived from the roots of *Paeonia lactillora* Pall, *Paeonia veitchii* Lynch and *P. suffrsticosa* Andrz of Ranuculaceae plants.

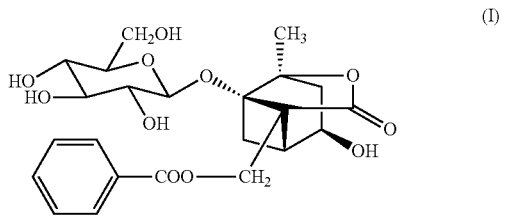

(I)

Albiflorin has a lactone ring structure, and does not have hemiacetal structure. It is converted into two products, paeonilactone A and paeonilactone B, under anaerobic conditions. The structures of paeonilactone A, paeonilactone B are shown as follows:

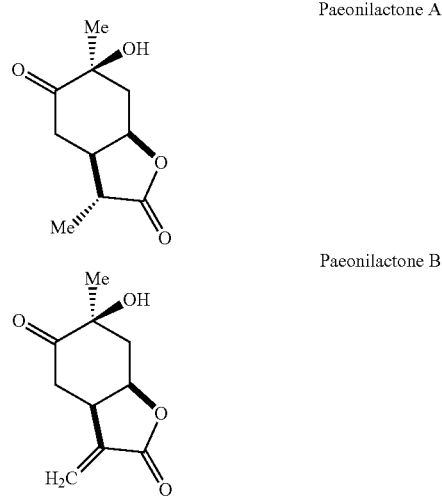

Modern pharmacological studies indicate that Albiflorin has analgesic, sedative, anticonvulsant effects, immune system-related effects, smooth muscle-related effects, anti-inflammatory effect, effects against pathogenic microorganisms, liver protective effect. Clinically speaking, Albiflorin is mainly used for the resistance to epilepsia, analgesia, drug abuse rehabilitation, the treatment of vertigo, the treatment of rheumatoid arthritis, the treatment of bacillary dysentery and enteritis, the treatment of viral hepatitis, the treatment of age-related diseases, the resistance to barium sulfate flocculation and mucus dissolution. The preparation method of Albiflorin and the use thereof in manufacturing the medicaments for the prevention and treatment of depression have not yet been reported.

According to lots of modern scientific research, the inventor employs advanced separation and purification techniques to extract the active ingredient Albiflorin from the crude drug *Radix paeoniae* for the treatment of depression, with making the content of Albiflorin above 50%. The inventor performs pharmacodynamically and pharmacologically anti-depressant studies on Albiflorin and corresponding formulation thereof, the results of which show that Albiflorin monomer has definite pharmacological effects, well-performed anti-depressant activity, low toxicity and side effects, high level of safety, and can be provided as a drug with high efficacy and low toxicity for the treatment of patients with depression.

SUMMARY OF THE INVENTION

For the existing problems in the prior art mentioned above, the primary object of the present invention is to provide the performance and effect of Albiflorin, Albiflorin metabolites, Albiflorin compositions, crude drugs comprising Albiflorin or extracts of crude drugs comprising Albiflorin for anti-mood disorders, especially anti-depression; meanwhile, for the existing problems in the prior art mentioned above, the present invention is to provide a novel medicinal use of Albiflorin, or the pharmaceutically acceptable salts or solvates thereof, or *Radix paeoniae* extract comprising an effective amount of Albiflorin, that is a novel use in the medicaments or food supplement for the treatment, recuperation and prevention of depression.

To achieve the above purpose, the present invention is to provide the use of Albiflorin in manufacturing the medicaments and food supplement for preventing, ameliorating and/or treating the diseases with mood disorders.

Wherein, said disease with mood disorder is depression.

In the process of screening natural active ingredients with anti-depressant effects, the inventor has found that, among the chemical components of *Radix paeoniae*, Albiflorin has a vigorous anti-depressant effect, and also has found that two metabolites of Albiflorin metabolized within the human bodies, paeonilactone A and paeonilactone B, also have anti-depressant effects.

Wherein, said "Albiflorin" refers to racemates, stereoisomers of Albiflorin, or mixture of stereoisomers mixed in any proportion.

Particularly, said "Albiflorin" also includes the two metabolites of Albiflorin, paeonilactone A and paeonilactone B.

Wherein, said medicaments consist of Albiflorin and pharmaceutically acceptable carriers.

Particularly, the pharmaceutically acceptable carriers are often accepted by the sanitarians to be intended for such purpose and used as inactive ingredients of medicaments. The assembly of the pharmaceutically acceptable carriers can be found in "Handbook of Pharmaceutical excipients, 2nd Edition, edited by A. Wade and P. J. Weller; published by American Pharmaceutical Association, Washington and The Pharmaceutical Press, London, 1994" and other reference books.

In particular, said carriers include excipients, such as starch, water and the like; lubricants, such as magnesium stearate and the like; disintegrating agents, such as microcrystalline cellulose and the like; fillers, such as lactose and the like; binders, such as pregelatinized starch, dextrin and the like; sweeteners; antioxidants; preservatives, flavoring agents, spices and the like;

Wherein, said medicaments are administered by gastrointestinal and parenteral administrations.

Particularly, said parenteral administration are selected from the group consisting of injection administration, respiratory tract administration, transdermal administration, mucosal administration or cavity administration.

Wherein, said medicaments are present in the form of tablets, capsules, pills, powders, granules, syrups, solutions, injections, sprays, aerosols, patches and the like.

Wherein, medicaments administered by parenteral routes are selected from the group consisting of injections, sprays, aerosols, patches and the like.

Particularly, said medicaments administered by gastrointestinal routes are selected from the group consisting of tablets, capsules, powders, pills, solutions, or syrups and the like.

Wherein, the purity of said Albiflorin is more than 50%, preferably more than 80%, further preferably more than 90%.

Wherein, the content of said Albiflorin is more than 50%, preferably more than 80%, further preferably more than 90%.

Another aspect of the present invention is to provide the use of Albiflorin compositions in manufacturing the medicaments and food supplement for preventing, ameliorating and/or treating the diseases with mood disorders.

Wherein, said disease with mood disorder is depression.

Wherein, said Albiflorin compositions are selected from the group consisting of pharmaceutically acceptable salts or solvates of Albiflorin.

Particularly, said pharmaceutically acceptable salts of Albiflorin are physiologically acceptable salts (especially, when being administered to humans and/or mammals as medicaments).

Wherein, said salts include the salts obtained by the addition of acids with Albiflorin. Said solvates of Albiflorin are Albiflorin hydrates.

Particularly, said acid is one or more acids selected from the group consisting of hydrochloric acid, fumaric acid, maleic acid, citric acid or succinic acid, these acids are only intended for illustrative purposes, without limiting the scope of the present invention.

Another aspect of the present invention is to provide the use of crude drugs comprising Albiflorin or extracts of crude drugs comprising Albiflorin in manufacturing the medicaments and food supplement for preventing, ameliorating and/or treating the diseases with mood disorders.

Wherein, said disease with mood disorder is depression.

Wherein, said crude drugs comprising Albiflorin are selected from *Radix paeoniae* or *Cortex mouton*, preferably *Radix paeoniae*. The purity of Albiflorin in said extracts of crude drugs comprising Albiflorin is more than 10%.

Another aspect of the present invention is to provide the use of Albiflorin metabolites in manufacturing the medicaments and food supplement for preventing, ameliorating and/or treating the diseases with mood disorders.

Wherein, said Albiflorin metabolites are selected from the group consisting of paeonilactone A, paeonilactone B; said disease with mood disorder is depression.

Particularly, said depression is one or more depressions selected from the group consisting of endogenous depression, reactive depression, postpartum depression, involutional melancholia, masked depression and depressive neurosis.

In particular, said depression is preferably reactive depression.

Still another aspect of the present invention is to provide medicaments comprising Albiflorin for preventing, ameliorating and/or treating depression.

Wherein, the purity of Albiflorin in said medicaments is more than 50%, preferably more than 80%, further preferably more than 90%.

Wherein, said medicaments also contain pharmaceutically acceptable carriers.

Still another aspect of the present invention is to provide medicaments for preventing, ameliorating and/or treating depression, which comprise at least one of the following substances: Albiflorin metabolites, Albiflorin compositions, crude drugs comprising Albiflorin or extracts of crude drugs comprising Albiflorin.

Wherein, said medicaments consist of one of the Albiflorin metabolites, Albiflorin compositions, crude drugs comprising Albiflorin or extracts of crude drugs comprising Albiflorin as well as pharmaceutically acceptable carriers.

Particularly, the purity of Albiflorin in said extracts of crude drugs comprising Albiflorin is more than 10%.

In particular, the purity of Albiflorin in said extracts of crude drugs comprising Albiflorin ranges from 10%~50%, preferably from 20%~45%, further preferably from 30%~40%.

Wherein, said Albiflorin metabolites are paeonilactone A, paeonilactone B.

Wherein, said Albiflorin compositions are selected from the group consisting of pharmaceutically acceptable salts or solvates of Albiflorin.

Particularly, said pharmaceutically acceptable salts of Albiflorin are physiologically acceptable salts (especially, when being administered to humans and/or mammals as medicaments).

Wherein, said salts include the salts obtained by the addition of acids with Albiflorin.

Particularly, said acids are one or more acids selected from the group consisting of hydrochloric acid, fumaric acid, maleic acid, citric acid or succinic acid, these acids are only intended for illustrative purposes, without limiting the scope of the present invention.

Wherein, said solvates of Albiflorin are Albiflorin hydrates.

Wherein, said crude drugs comprising Albiflorin are selected from *Radix paeoniae* or *Cortex moutan*, preferably *Radix paeoniae*.

Particularly, said carriers include excipients, such as starch, water and the like; lubricants, such as magnesium stearate and the like; disintegrating agents, such as microcrystalline cellulose and the like; fillers, such as lactose and the like; binders, such as pregelatinized starch, dextrin and the like; sweeteners; antioxidants; preservatives, flavoring agents, spices and the like;

Said medicaments can be prepared in to various formulations by means of the well-known methods in the field, such as tablets, capsules, pills, powders, granules, syrups, solutions, injections, sprays, aerosols, patches and the like.

Still another aspect of the present invention is to provide food supplement for preventing, ameliorating and/or treating depression, which comprise one of the following substances: Albiflorin, Albiflorin metabolites, Albiflorin compositions, crude drugs comprising Albiflorin or extracts of crude drugs comprising Albiflorin.

Wherein, the purity of said Albiflorin is more than 10%.

Particularly, the purity of Albiflorin in said extracts of crude drugs comprising Albiflorin ranges from 10%~50%, preferably from 20%~45%, further preferably from 30%~40%.

The present invention also provides a method for treating depression, which comprises administrating a therapeutically effective amount of Albiflorin pharmaceutical composition to the subjects, wherein the therapeutically effective amount thereof ranges from 0.6~4 mg/kg/d, preferably from 1~3.5 mg/kg/d, further preferably from 1.5~3 mg/kg/d.

Unless otherwise stated, the term "therapeutically effective amount" as defined herein refers to the amount of medicament intended for having desirable effect; "therapeutically effective amount" can be modified and changed, and finally determined by medical staff, the factors which should be taken into consideration include the routes of administration and formulation properties, body weights, ages and other general conditions of the subjects, as well as the properties and severity of the diseases to be treated Compared with the prior art, the present invention has the obvious advantages as follows:

1. The present invention explores the novel medicinal value of known compound Albiflorin as well as the pharmaceutically acceptable salts or solvates thereof, which is for the anti-depressant treatment (Albiflorin is of significance to shorten the immobility time of mice in the tail suspension test, and the immobility time of mice in the forced swimming test). Albiflorin can be prepared into medicaments or food supplement for the prevention, recuperation and/or treatment of depression in order to open up a new field for the application of *Radix paeoniae* and other crude drugs.

2. A series of experimental studies of the present invention show that Albiflorin has significant effect on prevention and treatment of depression, and is the active ingredient in peony and peony extract for the treatment of depression. Compared with the usually view that the paeoniflorin is the active ingredient in peony for the treatment of depression, Albiflorin has more significant effect to shorten the immobility time of mice in the tail suspension test, and the immobility time of mice in the forced swimming test, which indicates that the anti-depressant activity of Albiflorin is more effective than paeoniflorin.

3. The present invention performs a great deal of animal tests with different animal models using Albiflorin and the corresponding dosage forms by oral and injection administrations. The test results show that: (1) Albiflorin can significantly shorten the immobility time of mice in the tail suspension test and the immobility time in the forced swimming test, and it is in a significant dose-effect relationship; (2) Albiflorin can significantly reduce the reserpine-induced hypothermia; (3) Albiflorin can significantly inhibit the weight loss and reduced sucrose consumption of rats with chronic stress induced depression model, significantly reduce the number of errors of depressed rats in the jump on test, and significantly increase the horizontal and vertical movement scores of rats in open-field tests; (4) Albiflorin can significantly increase the contents of monoamine neurotransmitters, noradrenalin and serotonin, in the brains of depressed rats. From above, it is indicated that Albiflorin has a effective anti-depressant activity.

4. The Albiflorin of the present invention has a strong pharmacological activity, a significant effect on the prevention, recuperation and treatment of depression, quick onset of efficacy, low toxicity and side effects, and high level of safety. It can be administered for a long time, analyzed for the mechanism of anti-depressant activity thereof by modern pharmacology, and it is well available in the pharmaceutical field.

5. The product of the present invention has sufficient and low-cost sources of raw materials, high clinical safety, and simple preparing process. It can be prepared into various dosage forms, administered in a small dose, easily applied, and thus readily promoted.

6. According to the present invention, the active ingredient of Albiflorin can be not only independently prepared into the medicaments for the prevention and treatment of depression, but also can be prepared into the multi-target anti-depressants in combination with other active ingredients as formulations (for example, with ginsenoside Rg1, glycyrrhizic acid GL and other compounds).

DETAILED DESCRIPTION OF THE INVENTION

The present invention will be further described with the following examples. But these examples are only for illustrative purposes without limiting the scope of the present invention. In the following examples, the experimental methods without specifically indicated conditions are often in accordance with conventional conditions, or in accordance with the conditions recommended by the manufacturers.

The beneficial effects of said medicaments of the present invention will be further described by means of the following experimental examples. These experimental examples include the pharmacodynamic tests of the medicaments of the present invention.

EXPERIMENTAL EXAMPLE 1

Effect of Albiflorin on Mice in Tail Suspension Test 1.1 Experimental Materials

ICR mice, male, with the weight of 18~20 g, supplied by Vital River Experimental Animal Center, serial number of Certificate: SCXK (BJ) 2006-0009.

Albiflorin (purity: >98%), purchased from WAKO Corporation (Japan); Paeoniflorin (purity: >98%), purchased from National Institutes for Food and Drug Control (China); positive drug control: Fluoxetine Hydrochloride Capsules (Prozac), Lilly Suzhou Pharmaceutical Co., Ltd., batch number: A333341-070608.

JZ type 300 g tension transducer (Gaobeidian Xinhang electromechanical equipments Co., Ltd.), Medlab bio-signals acquisition and processing system (Nanjing Yimei Corporation).

1.2 Experimental Methods and Results

Normal mice were randomly divided into eight groups (n=20 for each group) according to their weights, i.e. model group, positive control group of fluoxetine hydrochloride capsules (3.5 mg/kg/d), high-dose group (14 mg/kg/d), medium-dose group (7 mg/kg/d), low-dose group (3.5 mg/kg/d) of Albiflorin, high-dose group (14 mg/kg/d), medium-dose group (7 mg/kg/d), low-dose group (3.5 mg/kg/d) of paeoniflorin. Each group was administered by gavage at a dose of 0.2 ml/10 g body weight, for two days.

In the second day, 1 h after the administration, the tail of mouse (2 cm away from the tip of the tail) was fixed to the connection line of 100 g tension transducer by adhesive plaster, and the mouse was hung upside down, with the head about 15 cm away from the experimental bench, two animals isolated from each other by a cardboard were simultaneously tested for each time. The transducer was connected to the Medlab bio-signals acquisition and processing system, after 2 min of adaption, the result over 4 min was recorded, and the immobility situation was converted into the time(s).

The experimental data were expressed as $\tilde{X} \pm SD$, and the analysis of variance for the experimental results was carried out by SPSS 11.5 statistical software (purchased from SPSS Inc., USA). The experimental results were shown in Table 1.

TABLE 1

Effect of Albiflorin on mice in tail suspension test ($\bar{x} \pm s$)

| Group | Dose (mg/kg) | n | Immobility Time (s) |
|---|---|---|---|
| Model | — | 20 | 93.47 ± 38.678 |
| Positive control | 3.5 | 20 | 66.21 ± 33.253* |
| High-dose of Albiflorin | 14 | 20 | 48.32 ± 32.756** |
| Medium-dose of Albiflorin | 7 | 20 | 65.12 ± 36.452* |
| Low-dose of Albiflorin | 3.5 | 20 | 83.82 ± 35.099 |
| High-dose of Paeoniflorin | 14 | 20 | 81.32 ± 32.756 |
| Medium-dose of Paeoniflorin | 7 | 20 | 76.83 ± 36.452 |
| Low-dose of Paeoniflorin | 3.5 | 20 | 85.62 ± 31.225 |

P.S.: compared with model group,
*$P < 0.05$,
**$P < 0.01$

As indicated in the experimental results:

1. The high- and medium-dose groups of Albiflorin all can significantly shorten the immobility time of mice in tail suspension test (compared with model group, $P<0.01$, $P<0.05$), and show a significant dose-effect relationship, which indicated that Albiflorin has a good anti-depressant function. The high- and medium-dose groups of Albiflorin are as effective as the positive control group, and the high-dose group of Albiflorin is significantly more effective than the positive control group.

2. The high-, medium- and low-dose groups of paeoniflorin also can shorten the immobility time of mice in the tail suspension test to a certain extent, however, compared with model group, they are not significantly different from the model group, which indicated that paeoniflorin has a weaker anti-depressant activity.

3. Albiflorin in peony extract has a significantly more effective anti-depressant activity than paeoniflorin, and is the major active ingredient of *Radix paeoniae* for the treatment of depression.

EXPERIMENTAL EXAMPLE 2

Effect of Albiflorin on Mice in Forced Swimming Test

2.1 Experimental Materials

ICR mice, male, with the weight of 18~20 g, supplied by Vital River Experimental Animal Center. Serial number of Certificate: SCX (BJ) 2006-0009.

Albiflorin (purity: >98%), purchased from WAKO Corporation (Japan); Paeoniflorin (purity: >98%), National Institutes for Food and Drug Control (China); positive drug control: Fluoxetine Hydrochloride Capsules (Prozac), Lilly Suzhou Pharmaceutical Co., Ltd., batch number: A333341-070608.

Thermometer, stopwatch, glass jar, Plato digital camera, portable computer.

2.2 Experimental Methods 160 normal mice were randomly divided into eight groups (n=20 for each group) according to their weights, i.e. model group, positive control group of fluoxetine hydrochloride capsules (3.5 mg/kg/d), high-dose group (14 mg/kg/d), medium-dose group (7 mg/kg/d), low-dose group of Albiflorin (3.5 mg/kg/d), high-dose group (14 mg/kg/d), medium-dose group (7 mg/kg/d), low-dose group (3.5 mg/kg/d) of paeoniflorin. Each group was administered by gavage at a dose of 0.2 ml/10 g weight, for two days, deionized water was administered to vehicle group.

In the second day, 1 h after the administration, the mice were placed separately into a water cylinder with 20 cm of height, 18 cm of diameter, 10 cm of depth, 23±2° C. of water temperature; observing each for 6 min, after 2 min of adaption, the immobility time over the last 4 min was recorded.

The data was expressed as x±s, analyzed by SPSS 13.0 statistical software by means of One-Way ANOVA test, the homogeneity of variance was tested by LSD and SNK test. The experimental results were shown in Table 2.

TABLE 2

Effect of Albiflorin on mice in forced swimming test ($\bar{x} \pm s$)

| Group | Dose (mg/kg) | n | Immobility Time (s) |
|---|---|---|---|
| Model | — | 20 | 64.90 ± 34.620 |
| Positive control | 3.5 | 20 | 30.05 ± 28.888* |
| High-dose of Albiflorin | 14 | 20 | 17.20 ± 24.230** |
| Medium-dose of Albiflorin | 7 | 20 | 33.65 ± 26.362* |
| Low-dose of Albiflorin | 3.5 | 20 | 44.85 ± 29.695 |
| High-dose of Paeoniflorin | 14 | 20 | 50.39 ± 31.257 |
| Medium-dose of Paeoniflorin | 7 | 20 | 43.94 ± 38.341 |
| Low-dose of Paeoniflorin | 3.5 | 20 | 58.60 ± 32.320 |

P.S.: compared with model group,
*$P < 0.05$,
**$P < 0.01$

As indicated in the experimental results:

1. The high- and medium-dose groups of Albiflorin all can significantly shorten the immobility time of mice in forced swimming test (compared with model group, P<0.01, P<0.05), which indicated that Albiflorin has a better anti-depressant activity, and shows a significant dose-effect relationship. The medium-dose group of Albiflorin is as effective as the positive control group, and the high-dose group of Albiflorin is significantly more effective than the positive control group.

2. The high-, medium- and low-dose groups of paeoniflorin also can shorten the immobility time of mice in the forced swimming test to a certain extent, however, compared with model group, they are not significantly different from the model group (P>0.05), which indicated that paeoniflorin has a weaker anti-depressant activity;

3. Albiflorin in peony extract has a significantly more effective anti-depressant activity than paeoniflorin, and is the major active ingredient of *Radix paeoniae* for the treatment of depression.

EXPERIMENTAL EXAMPLE 3

Effect of Albiflorin Administered by Intraperitoneal Injection on the Immobility Time of Mice in Tail Suspension Test

3.1 Experimental Materials

ICR mice, male, 18~20 g of weight, supplied by Vital River Experimental Animal Center.

Albiflorin (purity: 96.77%), purchased from Shanghai Forever-Biotech Co., Ltd.

JZ type 300 g tension transducer (Gaobeidian Xinhang electromechanical equipments Co., Ltd.), Medlab bio-signals acquisition and processing system (Nanjing Yimei Corporation).

3.2 Experimental Methods

Normal mice were randomly divided into three groups (n=20 for each group) according to their weights, i.e. model group, high-dose group (14 mg/kg) and medium-dose group (7 mg/kg) of Albiflorin. Intraperitoneal injection group was subjected to the administration for 1 day. Each group was administered at a dose of 0.2 ml/10 g weight.

The test of intraperitoneal injection group was performed at 30 min after the administration. The tail of mouse 2 cm away from the tip of the tail) was fixed to the connection line of 100 g tension transducer with adhesive plaster, and the mouse was hung upside down, with the head about 15 cm away from the experimental bench, two animals isolated from each other by a cardboard were simultaneously tested for each time. The transducer was connected into the Medlab bio-signals acquisition and processing system, after 2 mins of adaption, the result over 4 mins was recorded, and the immobility situation was converted into the time(s).

The experimental data was expressed as $\tilde{X} \pm SD$, and the analysis of variance for the experimental results was carried out by SPSS 11.5 statistical software (purchased from SPSS Inc., USA). The experimental results were shown in Table 3.

TABLE 3

Effect of Albiflorin administered by intraperitoneal injection on the immobility time of mice in tail suspension test ($\bar{x} \pm s$)

| Group | Dose (mg/kg) | n | Immobility time (s) |
|---|---|---|---|
| Model | — | 20 | 107.775 ± 53.3934 |
| High-dose of Albiflorin | 14 | 20 | 62.550 ± 40.1303** |
| Medium-dose of Albiflorin | 7 | 20 | 82.350 ± 52.5132 |

P.S.: compared with vehicle group,
P < 0.01**

As indicated in the experimental results: the high-dose group of Albiflorin administered by intraperitoneal injection can significantly shorten the immobility time of mice in tail suspension test (compared with model group, P<0.01**), which indicated that Albiflorin administered by intraperitoneal injection has a significant effect against the experimental depression.

EXPERIMENTAL EXAMPLE 4

Effect of Albiflorin on Mice in Reserpine-Induced Hypothermia Test

4.1 Experimental Materials

ICR mice, male, with the weight of 22.0±2 g, second class, purchased from Department of Experimental Animal Sciences, Capital Medical University, Beijing.

Albiflorin (purity: 96.77%), purchased from Shanghai Forever-Biotech Co., Ltd.; Paroxetine (Seroxat): produced by Tianjin SK&F Pharmaceutical Co., Ltd.; Reserpine: Guangdong Bangmin Pharmaceutical Co., Ltd.

GM222 type electronic thermometer, stopwatch.

4.2 Experimental Methods 50 mice were randomly divided into five groups (n=10 for each group): high-dose group (14 mg*kg$^{-1}$), medium-dose group (7 mg*kg$^{-1}$), low-dose group (3.5 mg*kg$^{-1}$) of Albiflorin; control group of paroxetine (3 mg/kg); model group of physiological saline. The gavage was carried out for 7 days.

Rectal temperatures of mice were measured at 1 hour after the administration on the 8th day, then reserpine was administered by intraperitoneal injection at a dose of 2 mg/kg, rectal temperatures of mice were measured again at 4 hours after the injection of reserpine. The depth into anus of thermometer and the time for each temperature measurement of mice was coincident.

The experimental data was expressed as $\tilde{X} \pm SD$, and the analysis of variance for the experimental results was carried out by SPSS 11.5 statistical software (purchased from SPSS Inc., USA), the experimental results were shown in Table 4.

TABLE 4

Effect of Albiflorin on mice in reserpine-induced hypothermia test

| Group | n | Hypothermia value (° C.) |
|---|---|---|
| Physiological saline (Model) | 10 | 3.65 ± 0.77 |
| Paroxetine (Positive control) | 10 | 2.38 ± 0.69** |
| High-dose group of Albiflorin | 10 | 0.97 ± 0.92** |
| Medium-dose group of Albiflorin | 10 | 2.34 ± 0.91** |
| Low-dose group of Albiflorin | 10 | 2.57 ± 0.67** |

P.S.: compared with model group,
*P < 0.05,
**P < 0.01

As indicated in the experimental results:

The high-, medium- and low-dose groups of Albiflorin as well as the positive control group (paroxetine group) all can significantly recede the reserpine-induced hypothermia, and have a significant difference (compared with model group, all are P<0.01**), which indicated that the effect thereof against the experimental depression may be related to the influence on the contents of monoamine neurotransmitters.

EXPERIMENTAL EXAMPLE 5

Effects of Albiflorin on the Body Weights and Behaviors of Mice with Chronic Stress Induced Depression

5.1 Experimental Materials

Male SD rats, with the weight of 240 g~260 g, purchased from Beijing Vital River Experimental Animal Center, serial number of Certificate: SCXK (BJ) 2002-0003.

Albiflorin (purity: >98%), purchased from WAKO Corporation (Japan); positive drug control: Prozac, Lilly Suzhou Pharmaceutical Co., Ltd., batch number: 20030017.

Sucrose, purchased from Beijing Guohua Chemicals Co., Ltd., batch number: 040120.

Drying oven, fixed cage for rats, hemostats, bucket, thermometer, the device for foot electric shock test, 1/100 second-scaled stopwatch, the open-field device for the observation of rat's behaviors, the device for jump on test.

5.2 Experimental Methods

After being fed without water for 24 hours, 90 normal rats were administered with 1% aqueous sucrose, the consumption was measured for 1 hour. Rats were randomly divided into six groups (n=15 for each group), i.e. vehicle group, model group, high-dose group (14 mg/kg/day), medium-dose group (7 mg/kg/day), low-dose group of Albiflorin (3.5 mg/kg/day), positive control group of Prozac (3 mg/kg/day). The gavage was carried out along with the model establishment, once a day, for 21 days. Each group was administered at a dose of 1.0 ml/100 g body weight, and the rats were weighed once a week.

Referring to the methods in the literature (Xu Jing, Li Xiaoqiu, Establishment and evaluation of the model of chronic stress induced depression, Chinese Journal of Behavioral Medical Science, 2003, 12(1): 14~16), the model was established (i.e., establishing animal model of anti-depression by means of CUMS): the foot electric shock (voltage: 36V, the electric shock is performed once every 1 minute, 10 seconds for once, 20 times in all), swimming in ice water at 4° C. (5 minutes), drying at 45° C. (5 minutes), tail nipping (1 min), wet feeding (wet mat), reversed day and night (24 hours), fasting (24 hours), water deprivation (24 hours) were randomly scheduled within 21 days, one kind of stimulations was given for each day, except for the animals of vehicle group, the others were separately caged with free diet, at the room temperature of (24±1)° C., with the relative humidity of (60±10)%.

5.2.1 Behavioral Observation

5.2.1.1 Consumption of Aqueous Sucrose

After each water deprivation, the consumptions of 1% aqueous sucrose for 1 hour of each animal group were measured.

5.2.1.2 Open-Field Test

The open-field device was of 40 cm in height, 80 cm in both length and width, without cap, the inner walls and the bottom of the device are black, and the bottom was divided into 25 squares with equal area. The numbers of squares that the animals pass through were designated as the score of horizontal movement, and the numbers of standing (with the forelegs above 1 cm away from the ground) were designated as the score of vertical movement. Each animal was measured for one time, 3 minutes for each measurement.

5.2.1.3 Jump Stair Test

The experimental device was a 30 cm×30 cm×30 cm plexi-glass box, the bottom of which had copper railings with spacing of 0.8 cm, it could be electrified with the voltage controlled by a transformer. A wooden platform (height: 5 cm, diameter: 8 cm) was placed into the box at the left back corner. Animals were placed into the response box to adapt to the environment for 3 minutes, and then the box was immediately electrified with 36V alternating current, the normal response of the animal which suffered from electric shock was to jump onto the platform in order to avoid such harmful stimulation. Most animals were likely to jump down to the copper railings again or for several times, and then quickly jump back to the platform after suffering from the electric shock, being trained like this for 5 minutes, the times that the rats suffered from the electric shock were designated as error times. The test was carried out again after 24 hours, rats were placed on the platform and the box was charged, timing and recording the error times for 5 minutes.

All parameters to be tested were expressed as Mean±SD ($\tilde{X}$±s), and tested by means of analysis of variance (ANOVA) in SPSS 12.0 software (purchased from SPSS Inc., USA), p<0.05 means that there was a significant difference.

5.3 Results

5.3.1 Effects of Albiflorin on the Body Weights of Mice with Chronic Stress Induced Depression As indicated in the results, on Day 0 and Day 7, there is not a significant difference in the weights of animals between each groups (P>0.05); on Day 14, compared with vehicle group, the weights of rats of model group are significantly reduced (P<0.01), and compared with model group, the weights of rats of medium-, high-dose groups of Albiflorin and of positive control group (Prozac group) are significantly increased (P<0.01); on Day 21, compared with vehicle group, the weights of rats of model group are significantly reduced (P<0.01), and compared with model group, the weights of rats of medium-, high-dose groups of Albiflorin and of positive control group (Prozac group) are significantly increased (P<0.01). The experimental results are shown in Table 5.

TABLE 5

Effect on the body weights of mice with chronic stress induced depression ($\bar{x} \pm s$, g)

| Group | Day 0 | Day 7 | Day 14 | Day 21 |
| --- | --- | --- | --- | --- |
| Vehicle | 249.72 ± 8.69 | 268.35 ± 11.95 | 313.08 ± 9.39** | 342.94 ± 11.56** |
| Model | 255.02 ± 10.43 | 261.88 ± 13.23 | 259.48 ± 12.25 | 265.48 ± 16.01 |
| Positice control | 257.19 ± 9.90 | 265.90 ± 13.94 | 280.64 ± 12.32** | 291.00 ± 11.31** |
| Low-dose | 256.83 ± 11.49 | 265.65 ± 11.23 | 270.75 ± 18.15 | 271.07 ± 19.06 |
| Medium-dose | 250.18 ± 13.45 | 265.65 ± 12.44 | 279.61 ± 15.99** | 294.01 ± 21.23** |
| High-dose | 255.84 ± 11.69 | 268.11 ± 17.50 | 277.05 ± 20.65** | 290.24 ± 19.11** |

P.S.: compared with model group,
*$P < 0.05$,
**$P < 0.01$,
***$P < 0.001$

5.3.2 Effect of Albiflorin on the Consumption of Aqeous Sucrose of Mice with Chronic Stress Induced Depression As indicated in the results, on Day 0 and Day 7, there is not a significant difference in the consumptions of aqueous sucrose of animals between each groups (P>0.05); on Day 14, compared with model group, the consumptions of aqueous sucrose of rats of medium-dose group of Albiflorin and of positive control group (Prozac group) are significantly increased (P<0.05); on Day 21, compared with vehicle group, the consumptions of aqueous sucrose of rats of model group are significantly reduced (P<0.05), and compared with model group, the consumptions of aqueous sucrose of rats of medium-, high-dose groups of Albiflorin and of positive control group (Prozac group) are significantly increased (P<0.01). The experimental results are shown in Table 6

TABLE 6

Effect of Albiflorin on the comsumption of aqeous sucrose of mice with chronic stress induced depression ($\bar{x} \pm s$, ml)

| Group | Day 0 | Day 7 | Day 14 | Day 21 |
| --- | --- | --- | --- | --- |
| Vehicle | 13.17 ± 6.97 | 11.17 ± 3.80 | 17.41 ± 7.30** | 16.91 ± 5.20** |
| Model | 13.17 ± 6.67 | 13.17 ± 7.21 | 10.00 ± 4.61 | 10.00 ± 2.76 |
| Positice control | 12.67 ± 5.53 | 10.00 ± 4.24 | 15.00 ± 2.22* | 14.91 ± 2.68** |
| Low-dose | 12.75 ± 5.24 | 12.67 ± 5.42 | 11.83 ± 5.15 | 11.92 ± 3.96 |
| Medium-dose | 12.67 ± 5.37 | 13.42 ± 5.37 | 14.25 ± 6.03* | 14.75 ± 5.14** |
| High-dose | 12.50 ± 5.32 | 14.08 ± 3.65 | 13.00 ± 3.74 | 14.50 ± 3.48** |

P.S.: compared with model group,
*$P < 0.05$,
**$P < 0.01$,
***$P < 0.001$

TABLE 7

Effect of Albiflorin on the behaviors of mice with chronic stress induced depression in open-field test ($\bar{x} \pm s$)

| Group | Score of horizontal movement | Score of vertical movement |
| --- | --- | --- |
| Vehicle | 45.91 ± 33.37* | 14.75 ± 11.50 |
| Model | 6.75 ± 2.49 | 1.75 ± 2.42 |
| Positice control | 28.09 ± 18.55* | 7.00 ± 3.90* |
| Low-dose | 21.42 ± 20.38 | 4.67 ± 6.87 |
| Medium-dose | 28.33 ± 18.63* | 6.50 ± 3.11** |
| High-dose | 29.25 ± 16.42** | 6.50 ± 3.37* |

P.S.: compared with model group,
*$P < 0.05$,
**$P < 0.01$,
***$P < 0.001$

5.3.3 Effect of Albiflorin on the Behaviors of Mice with Chronic Stress Induced Depression in Open-Field Test As indicated in the results, compared with vehicle group, the scores of horizontal and vertical movements of rats of model group are significantly reduced (P<0.05); compared with model group, the scores of horizontal and vertical movements of rats of medium-, high-dose groups of Albiflorin and of positive control group (Prozac group) are all significantly increased (P<0.05), see Table 7.

5.3.4 Effect of Albiflorin on the Behaviors of Mice with Chronic Stress Induced Depression in Jump Stair Test The results indicate that, compared with vehicle group, the error times of rats of model group in training period and in testing period are significantly increased (P<0.01); compared with model group, the error times of rats of medium-, high-dose groups of Albiflorin and of positive control group (Prozac group) in training period and in testing period are significantly reduced (P<0.05). The experimental results are shown in Table 8.

TABLE 8

Effect of Albiflorin on the error times of mice with chronic stress induced depression in jump stair test ($\bar{x} \pm s$)

| Group | Error times in training period | Error times in testing period |
|---|---|---|
| Vehicle | 1.83 ± 1.11** | 0.58 ± 0.67* |
| Model | 5.08 ± 1.83 | 3.16 ± 1.95 |
| Positive control | 2.09 ± 1.22** | 0.72 ± 1.19* |
| Low-dose | 2.25 ± 1.42 | 2.08 ± 1.31 |
| Medium-dose | 2.33 ± 1.37** | 0.67 ± 0.78* |
| High-dose | 2.33 ± 1.23** | 0.83 ± 0.94* |

P.S.: compared with model group,
*P < 0.05,
**P < 0.01,
***P < 0.001

5.4 Conclusion

Stress is one of the pathogenic factors of depression. The animal model established by means of using CUMS imitates the similar behavioral and neuroendocrine changes within human depression, and has become one of widely used animal model at home and abroad to explore the pathogenic mechanism of depression as well as the mechanism of action of anti-depressants. However, the stress models employed in the previous studies are mostly of a single form of stress, such as restraint stress, forced swimming and the like. To avoid the animals to adapt themselves to the identical stress, the present study employs a chronic stress model of multi-factors, different stress stimulations are randomly provided every day to act on the animals in order to make them unable to predict the times of onset and the types of stresses, and it is more closer to the mechanisms of onsets and developments of chronic and low-level stressor-induced depression in the human depressions. In combination with separate feeding on the basis of it, the environment of social animals is changed, which would ensure the success of model to a larger extent. With regard to the rats of model group, the scores of horizontal and vertical movements are significantly reduced, the consumptions of aqueous sucrose solution are obviously reduced, which indicated that the animals perform with depressed mood, loss of interest, reduced exploratory behavior, and anhedonia, and showed that the model of depressed rat is successfully established.

As indicated in the results of open-field test, jump stair test, and tests on body weights and consumptions of aqueous ssucrose, Albiflorin can effectively improve the depressed behaviors of rats of the depressed model, and have therapeutic effects on depression, as effective as positive control Prozac.

EXPERIMENTAL EXAMPLE 6

Effects of Albiflorin on the Monoamine Neurotransmitters in the Brains of Rats Suffered from Chronic Stress

6.1 Experimental Materials

Test drug: Albiflorin (purity: >98%), purchased from WAKO Corporation (Japan).

Positive control: fluoxetine hydrochloride (Prozac), Lilly Suzhou Pharmaceutical Co., Ltd., batch number: Chinese Drug Approval Number J20030017, the dosage for rats is 2.5 mg/kg.

Noradrenalin (NE, Serva Corporation); Dopamine (DA, Fluka Corporation); 5-hydroxyl tryptamine (5-HT, Sigma Corporation); 3,4-dihydroxyl phenylacetic acid (DOPAC, Sigma Corporation); 3,4-dihydroxyl benzylamine (DHBA, Sigma Corporation); di-n-butylamine (Shanghai Chemical Works), D-8 ion pair reagent (Tianjin Chemical Co., Ltd.), methanol (Guaranteed Reagent, Beijing Chemical Works), other reagents are domestically produced and analytically pure.

SD rats, male, with the weight of 220~240 g, supplied by Vital River Experimental Animal Center, serial number of Certificate: 2007-0001.

Waters 510 pump, M464 electrochemical detector, DL-822 chromatography workstation (National Chromatographic R. & A. Center, Dalian Institute of Chemical Physics), MSE150 type ultrasonic disintegrator.

6.2 Experimental Methods

6.2.1 Grouping and Administration

After being fed without water for 24 hours, SD rats were administered with 1% aqueous sucrose, the consumption of aqueous sucrose was measured for 1 hour. The rats were randomly divided into six groups (n=12 for each group) according to the consumptions of aqueous sucrose, i.e. vehicle group, model group, positive control group of Fluoroxetine Hydrochloride (2.5 mg/kg/d), high-dose group (14 mg/kg/day), medium-dose group (7 mg/kg/day), and low-dose group (3.5 mg/kg/day) of Albiflorin. The gavage was carried out along with the model establishment, once a day, for 21 days. Each group was administered at a dose of 1.0 ml/100 g weight, and weighed once a week.

6.2.2 Model Establishment

The rats were fed at 6/cage as vehicle group, with normal diets and drinking water, and without any stimulation.

The rats were fed at 1/cage as the other five groups, and subjected to unpredicted stress stimulations for 21 days, including: swimming in ice water, drying, tail nipping, wet feeding, reversed day and night, fasting, water deprivation and the like. One kind of stimulations was randomly given for each day.

Specific operation methods of each stress:

(1) Swimming in ice water: the animal was placed into bucket with cold water at 4° C. (mixed with ice and water), the depth of water was 15 cm, the rat just could touch the bottom of bucket with its toes, the animal was taken out 5 min later.

(2) Drying: the temperature of drying oven was adjusted and kept to 45° C., the animal was placed into drying oven and taken out 5 min later.

(3) Tail nipping: The rat was placed into the fixed cage with the tail outside, 1 cm away from the root of the tail was nipped with hemostat (the clamping force should not be excessive, that making the rat wail would be fine), lasting for 1 min (4) Wet feeding: at 8 o'clock in the morning, 200 ml of water was introduced into the rat cage, and the padding in the cage was replaced at 8 o'clock in the next morning.

(5) Reversed day and night: at 8 o'clock in the morning, the rat was placed into the dark box, and turned on the light to lighting at 8 o'clock in the evening, till 8 o'clock in the next morning.

(6) Fasting: the feeds were not available for 24 h.

(7) Water deprivation: the water was not available for 24 h.

6.2.3 Preparation and Determination of Samples

The animal was executed by decapitation, the brain of it was quickly stripped on the ice, the prefrontal cortex was taken out, then placed into frozen tissue tube after weighting, rapidly frozen with liquid nitrogen, and placed into the refrigerator at −70° C. until test.

According to the weight of brain tissue, pre-cooled 0.1 mol/L of perchloric acid (containing 0.3 mM EDTA disodium salt, and 0.5 mM sodium sulfite), 2 μg/ml DHBA were added and prepared to 800 μl, homogenized by ultrasonic, and centrifuged at 11000 rpm for 10 min, the supernatant was collected for the determination of the neurotransmitters.

The determination was performed using high performance liquid chromatography-electrochemical detection system (HPLC-ECD), the chromatographic conditions were: Novapak C18 column, 4×150 mm, 5 μm (packed by Dalian chromatographic R. & A. center); mobile phase was 50 mM citric acid-sodium acetate buffer at PH3.5 (containing 1.0 mM B-8 ion pair reagent, 1.8 mM di-n-butylamine, 0.3 mM EDTA disodium salt, 4% methanol); flow rate was 10 mL/min; vitreous carbon working electrode; voltage of detecting pool was +0.75V; internal standard was 3,4-dihydroxy benzylamine (DHBA), and the major ingredients in the sample were quantified by means of internal standard method.

The detection data was expressed as $\bar{X} \pm s$, analyzed by SPSS 13.0 software by means of One-Way ANOVA test, the results of detection were shown in Tables 9 and 10.

TABLE 9

Effect of Albiflorin on noradrenalin in the brain of rat with chronic stress ($\bar{x} \pm s$)

| Group | Dose (mg/kg) | n | NA |
|---|---|---|---|
| Vehicle | — | 12 | 398.47 ± 51.11* |
| Model | — | 10 | 159.20 ± 49.31 |
| Positive control | 2.5 mg/kg/d | 11 | 440.88 ± 62.58* |
| Low-dose | 3.5 mg/kg/d | 11 | 174.59 ± 60.35 |
| Medium-dose | 7 mg/kg/d | 11 | 345.19 ± 53.43* |
| High-dose | 14 mg/kg/d | 11 | 430.48 ± 52.50* |

P.S.: compared with model group,
*P < 0.05,
**P < 0.01

TABLE 10

Effect of Albiflorin on serotonin in the brain of rat with chronic stress ($\bar{x} \pm s$)

| Group | Dose (mg/kg) | n | 5-HT |
|---|---|---|---|
| Vehicle | — | 12 | 340.11 ± 75.88* |
| Model | — | 10 | 158.27 ± 60.34 |
| Positive control | 2.5 mg/kg/d | 11 | 272.19 ± 63.42* |
| Low-dose | 3.5 mg/kg/d | 11 | 188.43 ± 67.91 |
| Medium-dose | 7 mg/kg/d | 11 | 270.77 ± 56.43* |
| High-dose | 14 mg/kg/d | 11 | 288.86 ± 61.55* |

P.S.: compared with model group,
*P < 0.05,
**P < 0.01

As indicated in the experimental data of Tables 9 and 10, after consecutive administration for 21 days, compared with the vehicle group, the contents of monoamine neurotransmitters, noradrenalin and serotonin, in the rat brains of the model group are significantly reduced (P<0.05); compared with the model group, the contents of monoamine neurotransmitters, noradrenalin and serotonin, in the rat brains of the medium-, high-dose groups of Albiflorin and of positive control group of fluoxetine hydrochloride are significantly increased (P<0.05).

The functional deficiencies of the monoamine transmitters in brain, such as noradrenalin, serotonin, dopamine and the like, result in the onset of depression. The reason for the hypotensive effect of reserpine simultaneously accompanied with the initiation of depression is that reserpine causes the depletion of noradrenalin in the presynaptic membrane vesicles. The present experimental study has shown that the contents of serotonin and noradrenalin in the rat brain with chronic stress are significantly reduced, and Albiflorin can significantly increase the contents of serotonin and noradrenalin in the brain. It is indicated that the aforementioned effect may be one of the important mechanisms of anti-depressant activity of Albiflorin.

EXPERIMENTAL EXAMPLE 7

Effect of Extract of *Radix paeoniae alba* Comprising Albiflorin on the Immobility Time of Mice in Tail Suspension Test 7.1 Experimental Materials ICR mice, male, with the weight of 18~22 g, supplied by Vital River Experimental Animal Center, serial number of Certificate: 2007-0001.

Test drug: extract of *Radix paeoniae alba* comprising 31.16% of Albiflorin, provided by Beijing Wonner Biotech Co., Ltd.

Positive control: Fluoxetine Hydrochloride (Prozac), Lilly Suzhou Pharmaceutical Co., Ltd., batch number: Chinese Drug Approval Number J20030017, the dosage for mice was 3.5 mg/kg. The inclusions were taken out of the capsules, and prepared into solution with deionized water.

Medlab bio-signals acquisition and processing system (Nanjing Yimei Corporation), JZ100 type 100 g tension transducer (Gaobeidian Xinhang electromechanical equipments Co., Ltd.).

7.2 Experimental Methods and Results

Normal ICR mice were randomly divided into five groups, i.e. vehicle group, positive control group of fluoxetine hydrochloride (3.5 mg/kg/d), high-dose group (90 mg/kg/d), medium-dose group (45 mg/kg/d), low-dose group (22.5 mg/kg/d) of test drug. Each group was administered at a dosage of 0.2 ml/10 g body weight. The vehicle group was administered with deionized water by gavage once a day, for 2 days. The test was carried out at 1 hour after the last administration. The tail of mouse (2 cm away from the tip of the tail) was fixed to the connection line of 100 g tension transducer with adhesive plaster, and the mouse was hung upside down, with the head about 15 cm away from the experimental bench, the transducer was connected to the Medlab bio-signals acquisition and processing system, after 2 min of adaption, the immobility time(s) for 4 min was recorded.

The experimental data was expressed as $\bar{X} \pm s$, analyzed by SPSS 13.0 statistical software by means of One-Way ANOVA test. The experimental results were shown in Table 11.

TABLE 11

Effect on the immobility time of mice in tail suspension test

| Group | Dose (mg/kg/d) | n | Immobility time ($\bar{x} \pm s$) |
|---|---|---|---|
| Vehicle | — | 10 | 105.05 ± 8.91 |
| Positive control | 3.5 | 11 | 32.41 ± 4.54* |
| Low-dose of test drug | 22.5 | 10 | 91.10 ± 16.03 |

TABLE 11-continued

Effect on the immobility time of mice in tail suspension test

| Group | Dose (mg/kg/d) | n | Immobility time ($\bar{x} \pm s$) |
|---|---|---|---|
| Medium-dose of test drug | 45 | 10 | 30.80 ± 4.92* |
| High-dose of test drug | 90 | 10 | 60.90 ± 11.26* |

P.S.: compared with vehicle group,
*P < 0.05

As indicated in the experimental results, after administration by gavage for 2 days, the immobility time of mice of the high- and the medium-dose groups of test drug and the positive control group in tail suspension test are all significantly reduced, which is significantly different from the one of the vehicle group (P<0.05). It is indicated that the extract of Radix paeoniae alba comprising 31.16% of Albiflorin has a significant anti-depressant activity.

EXPERIMENTAL EXAMPLE 8

Acute Toxicity Test of Albiflorin

SFP level ICR mice were administered with Albiflorin at a dose of 8.4 g/kg, the observation time was 14 days.

The nature and rate of breath, behaviors (especially whether there was any vomit-causing phenomenon), actions, color and tension of fur, abdominal shape, hardness of feces, body weight and the like were observed.

After observation for 14 days, neither any abnormal symptom nor any death was found in animals; the body weight of mice of administering group were weighed on Day 7 and Day 14, respectively, without significant difference as compared with the vehicle group (P>0.05).

As indicated in the results of acute toxicity test, the mice were administered with Albiflorin by gavage, when the dosage reached up to 8.4 g/kg body weight (approximately 600 times as many as the clinical dosage), the medicaments of the present invention was still safe.

EXAMPLE 1

Preparation of Albiflorin Extract

Radix paeoniae alba was ground into powder, and heated to reflux in 70% ethanol aqueous solution for three times, the weights of solvents for these three times were 5 times, 4 times and 3 times, respectively, as many as the weight of Radix paeoniae alba (for example, for one kilogram of Radix paeoniae alba adding 5 kg of 70% ethanol aqueous solution), the ethanol was recovered, and the volume of extract was diluted up to 4 times (such as, for one kilogram of Radix paeoniae alba, the volume of diluted extract was 4 liters), and then the diluted extract was filtered to afford clarified solution A for further use.

D-101 type macroporous resin was immersed with 95% ethanol overnight, column was packed by means of wet method, and washed with water until nearly free of alcohol, the clarified solution was subjected to the D-101 type macroporous resin adsorption column, at a flow rate of 1 column volume/hour (BV/H) for adsorption, the column was firstly washed with 4 BV of water, then washed with 10% ethanol, and then eluted with 30% ethanol, the 2-5 BV of eluents were collected, concentrated and dried (temperature: ≤70° C., vacuum degree: ≤−0.06 Mpa), the residue was ground and sieved through a 80 mesh sieve to afford the Albiflorin extract with the content of 30~35%, the yield of extract was about 3~3.5%.

EXAMPLE 2

Preparation of Albiflorin Extract by Water Percolation

1) Radix paeoniae alba was crushed into coarse particles (≤10 mm), impregnated for 2 hours with 4 times amount of water as solvent (such as, one kilogram of Radix paeoniae alba was immersed with 4 kilograms of water), then the impregnation liquid was introduced into percolator, and immersed for 1 hour to percolate, at a flow rate of 0.03 ml/g·min, the amount of percolate (10 times as many as the amount of crude drug) was collected (such as, for 1 kilogram of Radix paeoniae alba, 10 kg of percolate was collected), the percolate was concentrated at atmospheric pressure until the ratio of concentrate to crude drug by weight was 2:1 (measured at 70° C.) to afford percolate A.

2) D-101 type macroporous resin was immersed with 95% ethanol overnight, column was packed by means of wet method, and washed with distilled water until nearly free of alcohol for further use.

3) The percolate A was subjected to the D-101 type macroporous resin adsorption column, the ratio of the amount of peony crude drug to the amount of resin was 1.5:1, at a flow rate of 0.033 ml/g·min, the eluate was discarded. The column was washed with water 3 times as many as the amount of resin, at a flow rate of 0.033 ml/g·min, the eluate is discarded. The column was washed with 50% ethanol 4 times as many as the amount of resin, at a flow rate of 0.033 ml/g·min, the eluate 4 times as many as the amount of resin was collected for further use. The column was washed with water until the content of ethanol in the eluate was 0%, the fraction eluted with 50% ethanol (loading solution) was repeatedly subjected to the column The eluate was concentrated under reduced pressure (temperature: ≤70° C., vacuum degree: ≤−0.06 Mpa), until the concentrated extract with the relative density of 1.30~1.35 (measured at 60° C.) was available, concentrated under reduced pressure (temperature: ≤70° C., vacuum degree: ≤−0.06 Mpa), the residues were ground and sieved through a 80 mesh sieve to afford the Albiflorin extract with the content of 30~55%, the yield of extract was about 4~5%.

Supplemented with auxiliary as required, the aforementioned Albiflorin, as the major anti-depressant active ingredient in the peony extract (Paeonia lactiflora Pall or Paeonia veitchii Lynch), was filled into capsules or prepared into tablets to afford the orally administered pharmaceutical composition preferred in the present invention; otherwise, the aforementioned peony extract (Paeonia lactiflora Pall or Paeonia veitchii Lynch) with high content of Albiflorin was formulated in combination with other anti-depressant active components (for example, ginsenoside, glycyrrhizic acid, glycyrrhetinic acid and the like) to provide the compound medicaments for the treatment of depression.

EXAMPLE 3

Preparation of Albiflorin Capsules 100 g of Albiflorin with the purity of 96.77% was mixed with 80 g of starch and 20 g of starch silica gel, then blended and directly filled into gelatin hard capsules to provide the capsules comprising 10 mg Albiflorin per capsule.

EXAMPLE 4

Preparation of Albiflorin Tablets 100 g of Albiflorin with the purity of 96.77% was ground, sieved through a 100 mesh sieve, and mixed with 700 g of starch pre-sieved through a 100 mesh sieve, a proper amount of starch slurry was added and well stiffed, the mixture was granulated through a 16 mesh sieve, dried below 60° C., pelletized, then a proper amount of magnesium stearate was added and well blended, the mixture was fed into pressure machine to press, and prepared into tablets comprising 10 mg Albiflorin per tablet.

EXAMPLE 5

Preparation of Albiflorin Sodium Chloride Injection 10 g of Albiflorin with the purity of 98.5% was added with 90 g of sodium chloride and water for injection, the mixture was stirred to be dissolved, water for injection was added until the volume reaches up to 1000 ml, and then the solution was filtered with 0.22 μm millipore filter, subdivided and sealed, sterilized for further use.

EXAMPLE 6

Preparation of Albiflorin Suspensions 200 g of peony extract with the Albiflorin content of 50% as prepared in example 2 was ground into granules with the particle size of 200 mesh, then added into 100 g of pre-swollen CMC and well stirred, distilled water was added until the volume reaches up to 10 L, the mixture was stirred to provide the suspension comprising 10 mg Albiflorin per milliliter suspension.

What is claimed is:

1. A method for ameliorating and/or treating reactive depression comprising administering to a subject in need thereof a medicament consisting of Albiflorin, pharmaceutically acceptable salts, solvates or metabolites of Albiflorin, and pharmaceutically acceptable carriers.

2. The method of claim 1, wherein the medicament is in the form of tablets, capsules, pills, powders, granules, syrups, solutions, injections, sprays, aerosols or patches.

3. The method of claim 1, wherein the Albiflorin metabolites are at least one of paeonilactone A and paeonilactone B.

* * * * *